(12) United States Patent
Cau et al.

(10) Patent No.: US 11,045,363 B2
(45) Date of Patent: Jun. 29, 2021

(54) FEMININE ABSORBENT ARTICLES WITH BONDED SIDE FLAPS AND AN APPARATUS FOR PRODUCING THE SAME

(71) Applicant: JOHNSON & JOHNSON CONSUMER INC., Skillman, NJ (US)

(72) Inventors: Jose Francisco Cau, São José dos Campos (BR); Marco Antonio Alkmin, São José dos Campos (BR); Gilson Philigret Sardinha, São José dos Campos (BR)

(73) Assignee: Johnson & Johnson Consumer Inc., Skillman, NJ (US)

( * ) Notice: Subject to any disclaimer, the term of this patent is extended or adjusted under 35 U.S.C. 154(b) by 655 days.

(21) Appl. No.: 15/939,965

(22) Filed: Mar. 29, 2018

(65) Prior Publication Data

US 2019/0298588 A1 Oct. 3, 2019
US 2021/0000663 A9 Jan. 7, 2021

Related U.S. Application Data

(60) Provisional application No. 62/479,812, filed on Mar. 31, 2017.

(51) Int. Cl.
*A61F 13/56* (2006.01)
*A61F 13/15* (2006.01)
(Continued)

(52) U.S. Cl.
CPC .... *A61F 13/5616* (2013.01); *A61F 13/15739* (2013.01); *A61F 13/15747* (2013.01);
(Continued)

(58) Field of Classification Search
CPC .......... A61F 13/15084; A61F 13/15756; A61F 13/15739; A61F 13/15747
See application file for complete search history.

(56) References Cited

U.S. PATENT DOCUMENTS 3,998,447 A 12/1976 Joa
4,900,320 A 2/1990 McCoy
(Continued)

FOREIGN PATENT DOCUMENTS

CN 105708624 A 6/2016
EP 581258 A 2/1994
(Continued)

OTHER PUBLICATIONS

International search report and written opinion dated Jul. 10, 2018, for international application PCT/US2018/025125.

*Primary Examiner* — Barbara J Musser

(57) ABSTRACT

A disposable sanitary napkin includes a main body and a pair of bridged flaps. The main body includes an absorbent system, a topsheet, and a backsheet, and it has a pair of side edges extending along the length thereof. The bridged flaps include a first straight edge, a second, shape-cut edge defining a projecting portion, and a bridging segment of a release liner having at least one zone of adhesive configured for attachment to the projecting portion of each bridged flap. Each bridged flap is attached to the main body with the first, substantially straight edge of each shaped strip aligned with a corresponding side edge of the main body, the bridged flaps are disposed over the topsheet, and each side flap is releasable from the bridging segment of the release liner.

2 Claims, 5 Drawing Sheets

(51) Int. Cl.
  *B29C 65/74* (2006.01)
  *B29C 65/48* (2006.01)
  *B29L 31/48* (2006.01)
  *A61F 13/60* (2006.01)

(52) U.S. Cl.
  CPC .. *A61F 13/15756* (2013.01); *A61F 13/15804* (2013.01); *B29C 65/4825* (2013.01); *B29C 65/74* (2013.01); *A61F 13/60* (2013.01); *B29L 2031/4878* (2013.01)

(56) References Cited

U.S. PATENT DOCUMENTS

| | | |
|---|---|---|
| 5,125,918 A | 6/1992 | Seidy |
| 5,201,727 A | 4/1993 | Nakanishi et al. |
| 5,800,654 A | 9/1998 | Davis et al. |
| 6,391,011 B1 | 5/2002 | Davis et al. |
| 6,447,495 B1 | 9/2002 | Luizzi et al. |
| 6,585,710 B1 | 7/2003 | Brisebois |
| 7,252,656 B2 | 8/2007 | Bonelli et al. |
| 8,048,050 B2 | 11/2011 | Cohen |
| 9,168,181 B2 | 10/2015 | Popp et al. |
| 2002/0007163 A1 | 1/2002 | Boulanger et al. |
| 2002/0156448 A1 | 10/2002 | Steger et al. |
| 2005/0124958 A1 | 6/2005 | Brisebois |
| 2005/0183814 A1 | 8/2005 | Alcantara et al. |
| 2012/0157279 A1 | 6/2012 | Schneider |
| 2014/0135730 A1 | 5/2014 | Mlinar et al. |
| 2015/0064387 A1 | 3/2015 | Imai et al. |
| 2015/0351978 A1 | 12/2015 | Langdon |

FOREIGN PATENT DOCUMENTS

| | | | |
|---|---|---|---|
| EP | 800807 A | 10/1997 | |
| EP | 1142546 A | 10/2001 | |
| EP | 2087868 A1 * | 8/2009 | ....... A61F 13/15756 |
| EP | 2275063 A | 1/2011 | |
| KR | 20110023781 A | 3/2011 | |
| WO | WO 1997/047265 A | 12/1997 | |
| WO | WO 1998/053781 A | 12/1998 | |
| WO | WO 2003/051255 A | 6/2003 | |
| WO | WO 2005/027782 A | 3/2005 | |

\* cited by examiner

FEMININE ABSORBENT ARTICLES WITH BONDED SIDE FLAPS AND AN APPARATUS FOR PRODUCING THE SAME

CROSS-REFERENCE TO RELATED APPLICATIONS

This application claims the benefit of U.S. provisional application 62/479,812 filed on Mar. 31, 2017.

FIELD OF THE INVENTION

The present invention relates to feminine absorbent articles with bonded side flaps. More specifically, the invention relates to a method of making feminine absorbent articles with bridging side flaps.

BACKGROUND OF THE INVENTION

Sanitary napkins are low cost mass produced articles. A typical manufacturing facility includes an assembly line where the various components of the sanitary napkin are progressively combined and laminated into a continuous web, which is cut transversely into discrete products.

The term "sanitary napkin", as used herein, refers to an article that is worn by females in their undergarments adjacent to the pudendal region and which is intended to absorb and contain the various exudates that are discharged from the body (e.g., blood, menses, vaginal discharges and urine). Hence, the term "sanitary napkin" encompasses pantiliners as well as catamenial devices. The term "disposable" refers to articles that are intended to be discarded after a single use. That is, the articles are not intended to be laundered or otherwise restored or reused as an absorbent article.

To enhance the functionality of sanitary napkins, manufacturers are designing products with complex and sophisticated contour lines. For example, it is known to provide sanitary napkins with flaps having adhesive disposed thereon, the flaps being adapted to be folded over and secured to the undergarment of the user via the adhesive, thereby enabling the secure attachment of the sanitary napkin to the undergarment. With traditional manufacturing techniques, extensive trimming is required to produce the highly irregular contoured edge of such sanitary napkins, which generates a considerable amount of waste material. As a result, the manufacturing cost of the sanitary napkin increases because the starting material is used less efficiently.

The industry has developed sanitary napkins with one or more flaps which can be produced with a reduced amount of waste material as compared to prior art sanitary napkins. Methods of manufacturing flapped absorbent articles where the flaps are bonded instead of making them from an extension of the product impermeable barrier and/or the cover layers are known to provide the advantage of reducing the amount of "scrap" in the end of the manufacturing process.

Such processes are also known to allow the production of flapped absorbent articles where the flaps are made from materials presenting properties that are not found in other product layers, and hence achieving a specific elasticity, air permeability or any other desired mechanical property which could not be achieved by simply making the flaps from an extension from the product impermeable barrier and/or the cover layers.

However, with the advantages in bonding the referred flaps comes increases in the complexity of manufacturing methods and apparatus. So, there is a need for a method and apparatus for manufacturing feminine absorbent articles including bonded flaps that is reduced in complexity.

Additionally, such processes are also known to be limited to produce absorbent articles having their longitudinal axis aligned with the machine's manufacturing direction, where such configuration is known to provide a reduced rate of production when compared to similar machines that manufactures the feminine absorbent articles having their longitudinal axis transversally oriented to the manufacturing direction. So, there is a need for a method and apparatus for manufacturing feminine absorbent articles including bonded flaps that manufactures those articles transversely oriented to the manufacturing direction.

Furthermore, there is a need for a method and apparatus for manufacturing feminine absorbent articles including bonded flaps that is reduced in complexity and that manufactures those articles transversely oriented to the manufacturing direction.

SUMMARY OF THE INVENTION

We have found novel methods for the improved manufacture of sanitary napkins having side flaps or wings.

In one embodiment, a method for manufacturing disposable sanitary napkins intended to be worn in an undergarment of a user includes the steps of forming pairs of bridged flaps, attaching the bridged flaps to a main body of the sanitary napkin, and enclosing the sanitary napkin in packaging material. The bridged flaps are formed by providing a continuous web having a longitudinal axis and at least a garment-facing layer and an opposite layer, bonding said superposed layers to form an area of juncture on said continuous web, said area of juncture defining a cyclic pattern and extending along said longitudinal axis, severing said continuous web within said area of juncture to form first and second shaped strips, adjusting the two shaped strips to align the projecting portions of the first shaped strip adjacent the projecting portions of the second shaped strip, whereby the adjusted shaped strips have outer edges defined by the first, substantially straight edges of the first and second shaped strips, applying zones of pressure sensitive adhesive to a continuous web of release liner, each zone of pressure sensitive adhesive corresponding to a projecting portion of the first and second shaped strips, and severing bridging segments of the release liner, each bridging segment having at least one zone of pressure sensitive adhesive arranged and configured for attachment to a projecting portion of the first shaped strip and at least one zone of pressure sensitive adhesive arranged and configured for attachment to a projecting portion of the second shaped strip, adjacent the projecting portion of the first shaped strip. Each strip has a first, substantially straight edge, a second, shape-cut edge defining a plurality of projecting portions in a spaced apart relationship, and at least one attachment portion disposed along the first edge between each of said projecting portions that unite said projecting portions to one another. The bridged flaps are attached to the main body in a manner such that the first, substantially straight edge of each shaped strip is aligned with a corresponding side edge of the main body, the bridged flaps are disposed over the topsheet, and each side flap is arranged and configured to be releasable from the bridging segment of the release liner and to be articulable away from the topsheet of the sanitary napkin and to be secured to a crotch portion of an undergarment for use. The main body of the sanitary napkin has a length, a width, and a thickness, includes an absorbent system, a topsheet, and a backsheet, and has a pair of side edges extending along the length thereof.

In one preferred embodiment, the bridged flaps are attached to the main body as the main body travels in a direction perpendicular to its length transverse to the disposable sanitary napkin.

In another embodiment, a disposable sanitary napkin intended to be worn in an undergarment of a user includes a main body and a pair of bridged flaps. The main body has a length, a width, and a thickness, and it includes an absorbent system, a topsheet, and a backsheet. The main body also has a pair of side edges extending along the length thereof. The bridged flaps include a first, substantially straight edge, a second, shape-cut edge defining a projecting portion, and a bridging segment of a release liner having at least one zone of pressure sensitive adhesive arranged and configured for attachment to the projecting portion of each bridged flap. Each bridged flap is attached to the main body such that the first, substantially straight edge of each shaped strip is aligned with a corresponding side edge of the main body, the bridged flaps are disposed over the topsheet, and each side flap is arranged and configured to be releasable from the bridging segment of the release liner and to be articulable away from the topsheet of the sanitary napkin and to be secured to a crotch portion of an undergarment for use.

DETAILED DESCRIPTION OF THE INVENTION

Figure 1:
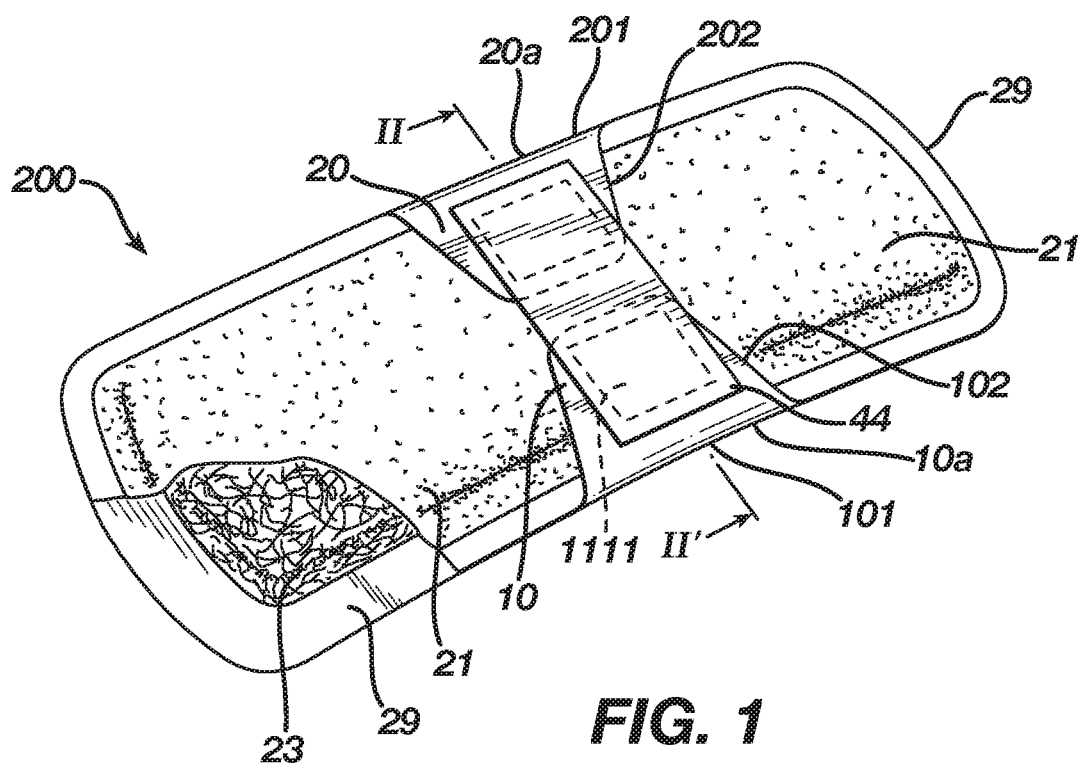
FIG. 1 is a perspective view of a feminine absorbent article made according to the present invention.
Figure 2:
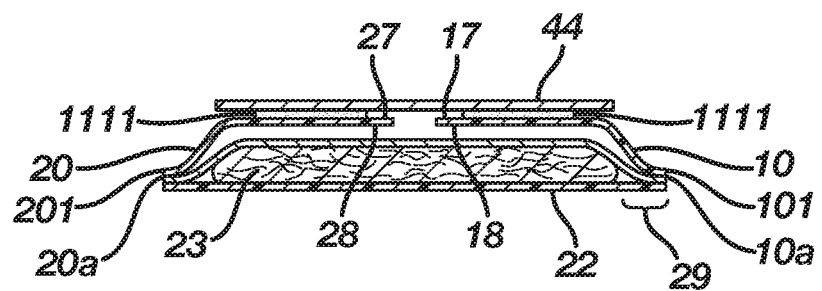
FIG. 2 is a cross-sectional view of the absorbent article of FIG. 1 along the II-II' plain.

FIGS. 1 and 2 show and embodiment of a feminine absorbent article 200 made according to the present invention. FIG. 1 is a perspective view of the absorbent article 200, while FIG. 2 is a cross-sectional view of the absorbent article of FIG. 1 along the II-II' plain. The feminine absorbent article 200 has a liquid-permeable topsheet 21, a liquid-impermeable backsheet 22 bonded to the topsheet 21, a liquid-absorbent core 23 disposed between the topsheet 21 and the backsheet 22. Feminine absorbent article 200 further includes a peripheral region 29 where the topsheet 21 and the backsheet 22 are bonded together.

Article 200 further includes a first side flap 10 and a second side flap 20. First side flap 10 and a second side flap 20 may also be referred to as first wing 10 and second wing 20. First side flap 10 has a first surface 17 and a second surface 18, as well as straight lateral edge 101 and shape-cut edge 102. Second side flap 20 has a first surface 27 and a second surface 28, as well as straight edge 201 and shape-cut edge 202. First side flap 10 is bonded to topsheet 21 along a region of first surface 17 adjacent to its straight lateral edge 101 in peripheral region 29. Likewise, second side flap 20 is bonded to topsheet 21 along a region of first surface 27 adjacent to its straight edge 201 in peripheral region 29. The bonding means for bonding first side flap 10 and second side flap 20 to peripheral region 29 may include an adhesive weld, a heat weld, or an ultrasonic weld. The bonding of the first side flap 10 to the peripheral region 29 and the second side flap 20 to the peripheral region 29 forms flanges 10a, 20a adjacent the straight lateral edges 101, 201. In one embodiment, shown in FIG. 9, the bonding means is a layer of adhesive 1221.

Second surface 18 of first side flap 10 includes a region with fastening adhesive 1111, as does second surface 28 of second side flap 20. First side flap 10 and second side flap 20 are folded over topsheet 21, and are releasable bonded by a discrete piece of a release liner 44 placed on each layer of fastening adhesive 1111. The fastening adhesive may be any adhesive known to those of ordinary skill in the art, including without limitation, hot melt adhesives and solvent-based adhesives.

Figure 3:
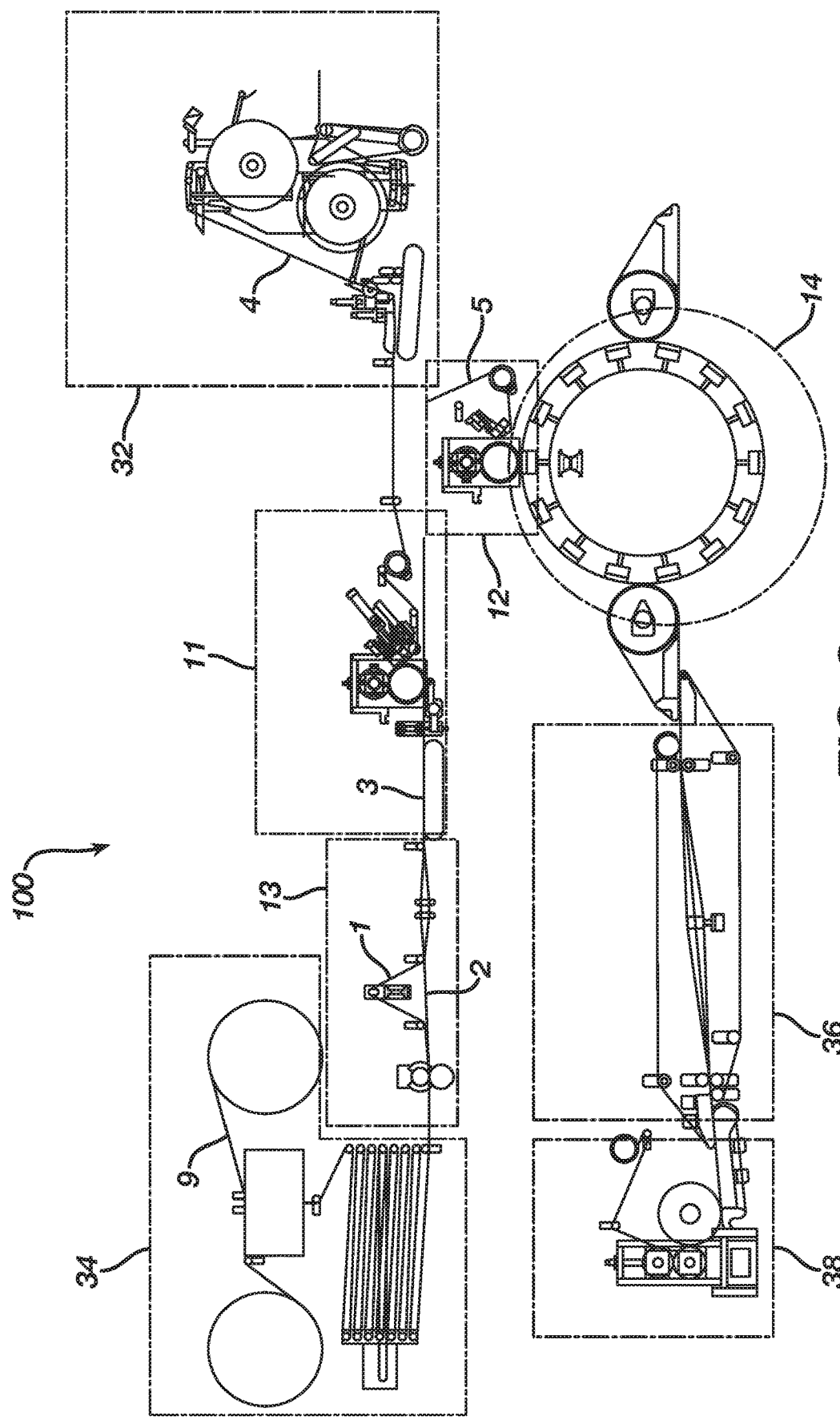
FIG. 3 is a descriptive schematic of the apparatus of the present invention.

FIG. 3 is a descriptive schematic of the apparatus 100 of the present invention. Apparatus 100 includes a release paper unwinder system 32, a wing material unwinder system 34, a wing synchronizer station 13, a release liner cut and place station 11, a flap kit maker 12, a rotary wheel 14, a twister 36, and a die cutter 38.

The release paper unwinder system 32 is aimed to properly feed the apparatus with the release liner 4 to the apparatus and further obtaining discrete pieces of release liner 44. It typically comprises a set of unwinder rolls and tensioning means.

The set of unwinder rolls uses two servo driven shafts and gripping means to engage the shaft inside the roll of release lines 4 (as a rolled starting material). The gripping means may consist of mechanic of pneumatic elements on the shaft.

The speed of the unwinding rolls is preferentially controlled by a PLC which manages their rotation speed by instantaneously reading the roll diameter.

An automatic splice unit works in synchronism with the unwinders allowing a perfect splicing from one roll to the next one at production speed and with the smallest waste of raw material. This unit uses pneumatic cylinders, vacuum conveyor, knives and pressing rolls. The automatic splicing starts by a signal from the roll sensors to the PLC informing that the minimum diameter has been achieved by the roll which is in use. In this moment, the vacuum conveyor receives a message from the PLC to starts feeding the raw material from the new roll. At the same time the roll which is in use stops.

The tensioning means may consist of a set of rolls or a vacuum featured conveyor. Preferentially it will be selected from a vacuum conveyor system, taking in consideration the mechanical properties of the release paper 4.

The wing material unwinder system 34 is aimed to properly feed the apparatus with the single strip 9 that will further be turned in side flaps 10/20. Similarly to the release paper unwinder system 32, the wing material unwinder system 34 typically comprises a set of unwinder rolls and tensioning means. Due to the mechanical properties of the single strip 9, the selected tension means may include a festoon, which will store some release liner 9 that will be consumed during the change of unwinder rolls.

The wing synchronizer station 13 is used as a means for managing the substrate strip 9 used to form first wing 10 and second wing 20. Suitable means for managing substrate strip 9 are known in the art; typically, they consist of an arrangement, a station, capable of splitting a single substrate strip 9 in two strips. The strips have a non-linear cut, providing shaped substrate strips having a straight lateral edge 101 and a shape-cut edge 102 which are used to construct side flaps 10 and 20.

An exemplary arrangement for manufacturing shaped strips is described in the published U.S. Pat. US2005/0124958, where all the content of its disclosure is herein incorporated by reference.

Typically, wing synchronizer station 13 includes cutting means like knives to split single substrate strip 9 into a first strip 1 and a second strip 2. Wing synchronizer station 13 also includes a series of spacer elements to move longitudinal and transversally first strip 1 in relation to second strip 2 to assisting the desired placement of the strips onto the products, in a further step of the process.

Figure 4:
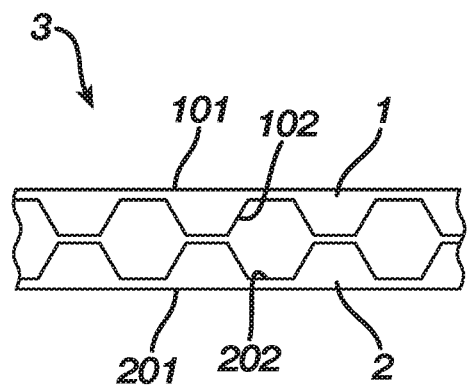
FIG. 4 is a top view of a pair of strips as they transition from the wing synchronizer station to the release liner cut and place station.

FIG. 4 is a top view of a pair of strips 3 as they transition from the wing synchronizer station 13 to the release liner cut and place station 11. Wing synchronizer station 13 will result in first strip 1 and second strip 2. First strip 1 has a substantially straight lateral edge 101 and a shape-cut edge 102, as well as first surface 17 and a second surface 18. Second strip 2 has a substantially straight lateral edge 201 and a shape-cut edge 202, as well as first surface 27 and a second surface 28. Shape-cut edge 102 and shape-cut edge 202 are symmetrically oriented along an imaginary longitudinal line.

Figure 5:
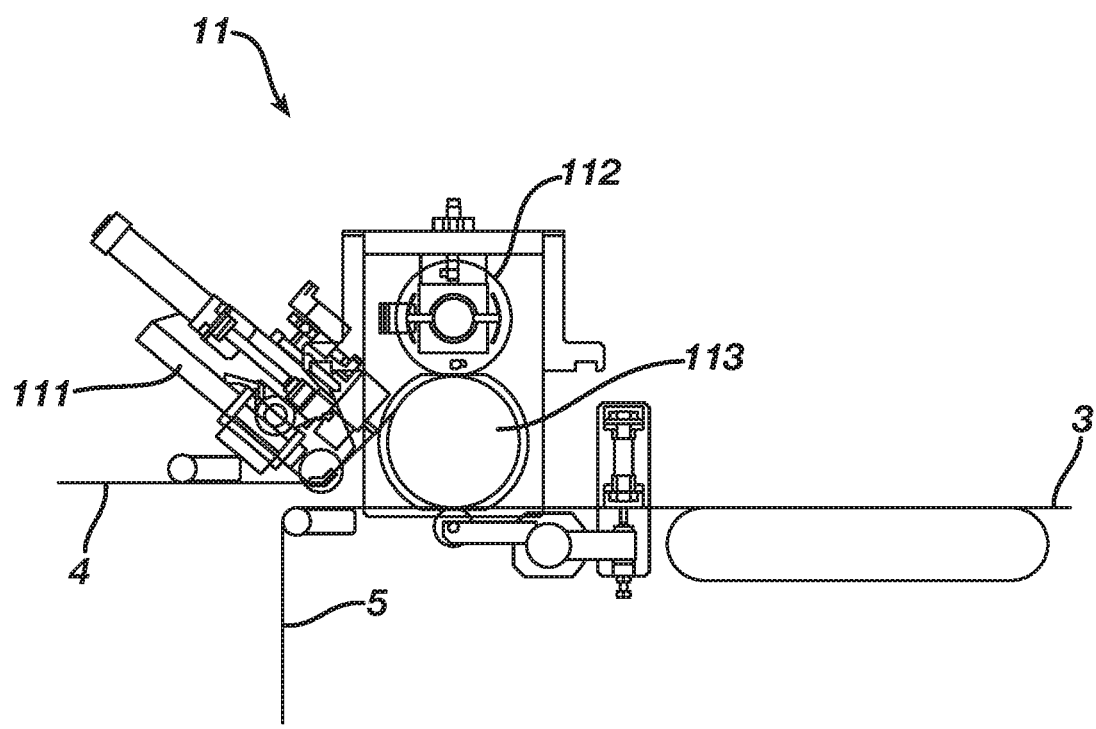
FIG. 5 is a schematic of the release liner cut and place station.
Figure 6:
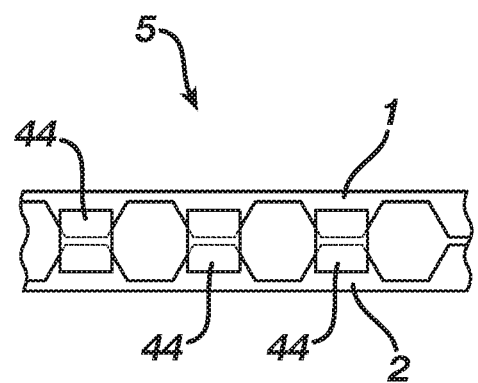
FIG. 6 is a top view of strip of bridged flaps as they transition from the release liner cut and place station to the flap kit maker.

FIG. 5 is a schematic of the release liner cut and place station 11. Release liner cut and place station 11 is fed with a pair of strips 3 obtained from the wing synchronizer station 13 and a continuous strip of release liner 4 obtained from release paper unwinder system 32. Release liner cut and place station 11 converts pair of strips 3 and continuous strip of release liner 4 obtained into a unitary strip 5 as shown in FIG. 6.

Release liner cut and place station 11 includes a hot melt adhesive applicator 111, knife 112, and vacuum featured roll 113.

Hot melt adhesive applicator 111 is used to apply hot melt adhesive 1111 onto continuous release liner strip 4. There are several suitable adhesive applicators to the present invention, from contactless applicators to contact applicators. Contactless applicators which may be used in some embodiments, are those which sprays the adhesive, such those found in the PATERN JET spray applicators, or SPEEDCOAT slot applicators, supplied from Nordson Corporation (Westlake, Ohio). Contact applicators, which may be used in some embodiments, are like those found in the TRUECOAT line of applicators, supplied from Nordson Corporation (Westlake, Ohio).

Knife 112 used in release liner cut and place station 11, is preferentially a roll kind of knife that cooperates with vacuum featured roll 113 to create a cutting nip where the release liner 4 will be cut and converted into discrete pieces of release liner 44. Once leaving the cutting nip, discrete pieces of release liner 44 are conveyed to pair of strips 3 by vacuum featured roll 113. Once the discrete pieces of release liner 44 leave vacuum featured roll 113, they will remain releasable bonded to pair of strips 3 by the hot melt adhesive 1111. As a result, pair of strips 3 shown in FIG. 3 are converted into a unitary strip 5 shown in FIG. 6. Preferentially, some pressure will be performed by vacuum featured roll 113 when transferring the discrete pieces of release liner 44 to pair of strips 3, in order to achieve bonding strength between them.

Release liner cut and place station 11 is further capable of selectively separating one discrete piece of release liner 44 from another, in order to place them onto pair of strips 3 in such way to bridge pair of strips 3 by means of hot melt adhesive 1111. Separation and bridging is accomplished by managing the tangential speed of vacuum featured roll 113, where typically a servo-mechanical system is capable of controlling such tangential speed.

It is important to note that discrete pieces of release liner 44 are moved from the cutting nip to pair of strips 3 by the vacuum featured roll 113 because of how its vacuum chambers are configured. A specialist in such kind of machines will be able to properly decide where to place the vacuum chambers, in order to properly convey discrete pieces of release liner 44, until placing them onto pair of strips 3. FIG. 6 shows a unitary strip 5 of bridged flaps as they transition from release liner cut and place station 11 to the flap kit maker 12. The figure shows a unitary strip 5 of bridged flaps connected by discrete pieces of release liner 44.

Figure 7:
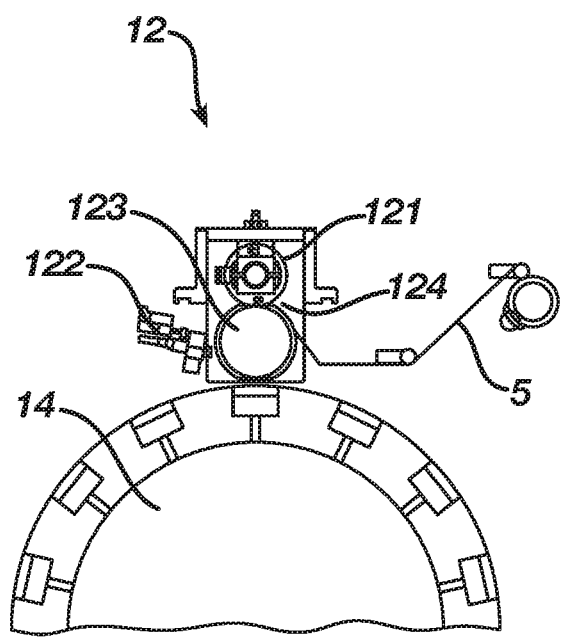
FIG. 7 is a schematic of the flap kit maker.
Figure 8:
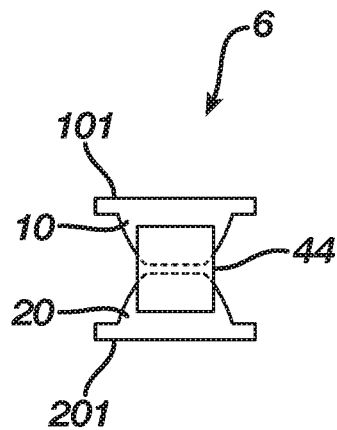
FIG. 8 is a top view of unitary flap kit.

FIG. 7 is a schematic of the flap kit maker 12. Flap kit maker 12 converts continuous strip 5 of bridged flaps into discrete unitary bridged flap kits 6, with each bridged flap kit 6 consisting of a pair of side flaps (first side flap 10 and second side flap 20) releasable bonded by a single discrete piece of release liner 44 by pressure sensitive hot melt adhesive 1111. FIG. 8 is a top view of a unitary bridged flap kit 6 upon exit from flap kit maker 12. Unitary bridged flap kit 6 has first side flap 10 and second side flap 20 bridged and connected by discrete piece of release liner 44.

Flap kit maker 12 included a knife 121 and a vacuum featured wheel 123. Knife 121, preferentially a roll kind of knife, cooperates with vacuum featured wheel 123 to create a nip 124 where unitary strip 5 of bridged flaps will be cut and converted into separate unitary bridged flap kit 6.

In the embodiment shown, flap kit maker 12 includes a hot melt adhesive applicator 122 aimed to apply hot melt adhesive 1221 onto second surface 18 of first side flap 10 adjacent to straight lateral edge 101 and onto second surface 28 of second side flap 20 adjacent to straight edge 201.

Figure 9:
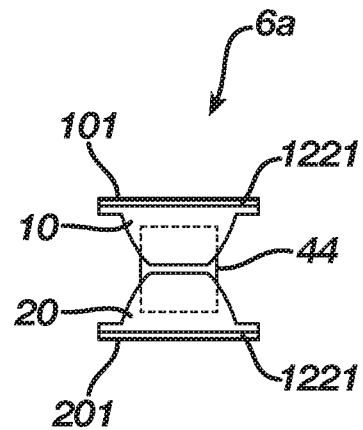
FIG. 9 is a bottom view of unitary flap kit upon exit from the flap kit maker.

FIG. 9 is a bottom view of unitary flap kit 6a upon exit from flap kit maker 12. The figure shows the location of hot melt adhesive 1221 on second surface 18 of first side flap 10 and second surface 28 of second side flap 20.

Figure 10:
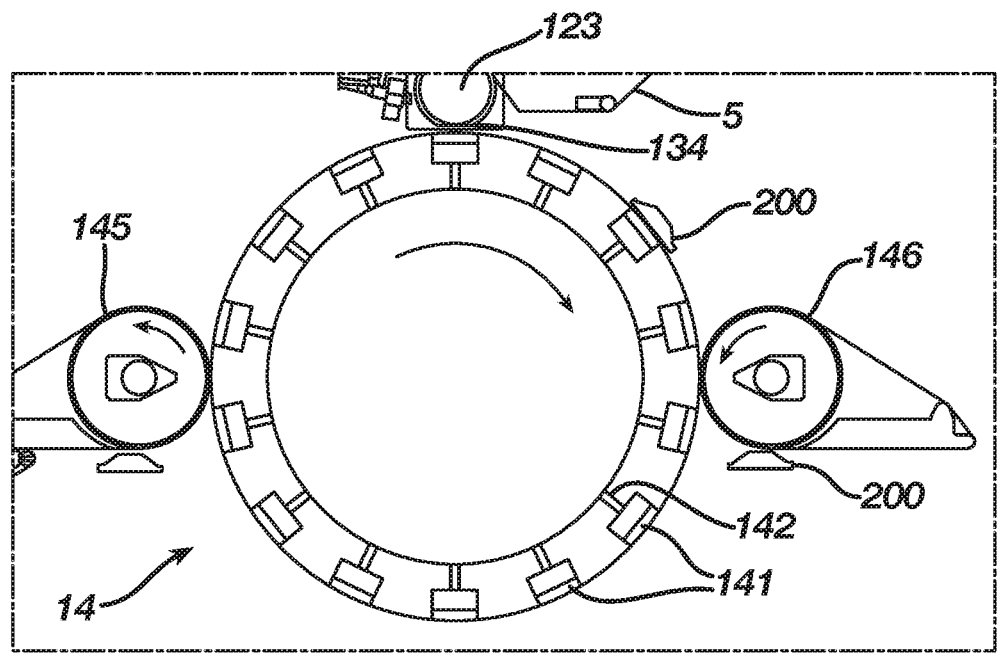
FIG. 10 is a schematic of the rotary wheel.

FIG. 10 is a schematic of rotary wheel 14 for use in the present invention. Rotary wheel 14 cooperates with flap kit maker 12 to transfer and bond unitary flap kits 6a onto the absorbent articles. In this sense, rotary wheel 14 and vacuum featured wheel 123 of flap kit maker 12 cooperate creating a nip 134 which selectively compress a unitary flap kit 6a against an absorbent article; both rotary wheel 14 and the vacuum featured wheel 123 include vacuum chambers selectively arranged to promote the transfer of each unitary flap kit 6a to a respective absorbent article. In particular product embodiments, the rotary wheel may apply more than a single unitary flap kit 6a per product, which is typically found on overnight products.

In embodiments where unitary flap kit 6a includes hot melt adhesive 1221 applied by adhesive applicator 122 of flap kit maker 12 on second surface 18 of first side flap 10 adjacent to straight lateral edge 101 and on second surface 28 of second side flap 20 adjacent to straight edge 201, it will permanently bond unitary flap kit 6a to the peripheral region 29 of feminine absorbent article 200 once article 200 has left nip 134.

Depending on the orientation of the manufactured absorbent articles 200 in relationship to the machine's manufacturing direction, the longitudinal axis of flap kit 6a might not be aligned with the longitudinal axis of absorbent articles 200. In such cases, rotary wheel 14 can rotate absorbent articles 200 before they reach nip 134, if featured with vacuum featured shoe 141.

One exemplary rotation mean is a geared vacuum featured shoe 141. As seen in FIG. 10, geared vacuum featured shoe 141 is connected to a vacuum source by a pneumatic connection 142. Thus, a geared vacuum featured shoe 141 is capable of sticking to absorbent articles 200 and rotating them.

Preferentially, the absorbent articles will be conveyed from a feeding tray 145 to rotary wheel 14 and from rotary wheel 14 to collecting tray 146 by means of vacuum forces.

The twister 36 has two flat conveyors which are independently servo driven and have the function of receiving absorbent article 200 from the conveyors after the final cut and turn it 180 degrees from the original position making the bottom surface of the product assumes the top position (absorbent article 200 is turned upside down). After being turned, absorbent article 200 is delivered to the conveyor belt (feeding tray 145) and then to the rotary wheel 14.

The die cutter 38 does the final cut of the product to the final dimensions and configuration (product contour). This operation, final cut, is done using a pair of rotary tools (knife and anvil) which runs together and cut absorbent article 200 by squeezing. The cutting force is applied to the tool by pneumatic, hydraulic or mechanical actuators. The design waste is removed from this station by pneumatic transportation. The pair, knife and anvil, is done of hard materials and can be submitted to an operation of re-sharpening in order to recover its ability of cutting smoothly.

The disposable sanitary napkins intended to be worn in an undergarment of a user may be manufactured by forming pairs of bridged flaps, attaching the bridged flaps to the main body of the sanitary napkin, and enclosing the sanitary napkin in a packaging material. The main body has a length, a width, and a thickness, and it includes an absorbent system disposed between a topsheet, and a backsheet. The main body has a pair of side edges extending along the length thereof. The bridged flaps are formed from a continuous web having a longitudinal axis and at least a garment-facing layer and an opposite layer. These two layers are superposed to form an area of juncture on said continuous web, said area of juncture defining a cyclic pattern and extending along said longitudinal axis. The continuous web is severed within said area of juncture to form first and second shaped strips. Each shaped strip has a first, substantially straight edge, a second, shape-cut edge defining a plurality of projecting portions in a spaced apart relationship, and at least one attachment portion disposed along the first edge between each of said projecting portions that unite said projecting portions to one another.

The two shaped strips are adjusted to align the projecting portions of the first shaped strip adjacent the projecting portions of the second shaped strip. Thus, the adjusted shaped strips have outer edges defined by the first, substantially straight edges of the first and second shaped strips. Zone of pressure sensitive adhesive are applied to a continuous web of release liner, each zone of pressure sensitive adhesive corresponding to a projecting portion of the first and second shaped strips. The resulting structure is severed to provide bridging segments; having at least one zone of pressure sensitive adhesive arranged and configured for attachment to a projecting portion of the first shaped strip and at least one zone of pressure sensitive adhesive arranged and configured for attachment to a projecting portion of the second shaped strip, adjacent the projecting portion of the first shaped strip.

The bridging segment is attached to the main body as follows: the first, substantially straight edge of each shaped strip is aligned with a corresponding side edge of the main body and affixed thereto with a flange seal 10a, 20a, the bridged flaps are disposed over the topsheet, and each side flap is arranged and configured to be releasable from the bridging segment of the release liner. The side flaps are also arranged and configured to be articulable away from the topsheet of the sanitary napkin and to be secured to a crotch portion of an undergarment for use whereby the flange seals 10a, 20a are disposed inwardly toward the crotch portion of the undergarment.

While the foregoing description and drawings represent exemplary embodiments of the present invention, it will be understood that various additions, modifications and substitutions may be made therein without departing from the spirit and scope of the present invention. The presently disclosed embodiments are therefore to be considered in all respects as illustrative and not restrictive, the scope of the invention being indicated by the appended claims, and not limited to the foregoing description.

What is claimed is:

1. A method for manufacturing disposable sanitary napkins intended to be worn in an undergarment of a user, said method comprising:
   (a) forming pairs of bridged flaps comprising the steps of
      (i) providing a continuous web having a longitudinal axis and at least a garment-facing layer and an opposite layer;
      (ii) bonding said superposed layers to form an area of juncture on said continuous web, said area of juncture defining a cyclic pattern and extending along said longitudinal axis;
      (iii) severing said continuous web within said area of juncture to form first and second shaped strips, each strip having:
         (A) a first, substantially straight edge;
         (B) a second, shape-cut edge defining a plurality of projecting portions in a spaced apart relationship;
         (C) at least one attachment portion disposed along the first edge between each of said projecting portions that unite said projecting portions to one another;
      (iv) adjusting the two shaped strips to align the projecting portions of the first shaped strip adjacent the projecting portions of the second shaped strip, whereby the adjusted shaped strips have outer edges defined by the first, substantially straight edges of the first and second shaped strips;
      (v) applying zones of pressure sensitive adhesive to a continuous web of release liner, each zone of pressure sensitive adhesive corresponding to a projecting portion of the first and second shaped strips;
      (vi) severing bridging segments of the release liner, each bridging segment having at least one zone of pressure sensitive adhesive arranged and configured for attachment to a projecting portion of the first shaped strip and at least one zone of pressure sensitive arranged and configured for attachment to a projecting portion of the second shaped strip, adjacent the projecting portion of the first shaped strip; and (vii) attaching bridging segments of the release liner to projecting portions of the first and second shaped strips to form the pairs of bridged flaps;

(b) forming a main body of a sanitary napkin, the main body:

(i) having a length, a width, and a thickness;

(ii) comprising an absorbent system, a topsheet, and a backsheet; and (iii) having a pair of side edges extending along the length thereof;

(c) attaching the bridged flaps to the main body wherein the first, substantially straight edge of each shaped strip is aligned with a corresponding side edge of the main body, the bridged flaps are disposed over the topsheet, and each side flap is arranged and configured to be releasable from the bridging segment of the release liner and to be articulable away from the topsheet of the sanitary napkin and to be secured to a crotch portion of an undergarment for use; and (d) enclosing the sanitary napkin in a packaging material.

2. The method of claim 1 wherein the step of attaching the bridged flaps to the main body occurs as the main body is disposed on a support and travels in a direction perpendicular to its length transverse to the disposable sanitary napkin.

\* \* \* \* \*